United States Patent [19]

Joerg et al.

[11] Patent Number: 5,194,675
[45] Date of Patent: Mar. 16, 1993

[54] PREPARATION OF METHYL FORMATE

[75] Inventors: Klaus Joerg, Limburgerhof; Franz-Josef Mueller, Wachenheim; Matthias Irgang, Heidelberg; Laszlo Marosi; Gerhard Borchert, both of Ludwigshafen, all of Fed. Rep. of Germany

[73] Assignee: BASF Aktiengesellschaft, Ludwigshafen, Fed. Rep. of Germany

[21] Appl. No.: 819,590

[22] Filed: Jan. 9, 1992

Related U.S. Application Data

[63] Continuation of Ser. No. 606,324, Oct. 31, 1990, abandoned.

[30] Foreign Application Priority Data

Nov. 6, 1989 [DE] Fed. Rep. of Germany ....... 3926854

[51] Int. Cl.$^5$ ............................................. C07C 67/00
[52] U.S. Cl. .................................................... 560/239
[58] Field of Search ......................................... 560/239

[56] References Cited

U.S. PATENT DOCUMENTS

| 1,400,195 | 12/1921 | Willkie | 560/239 |
| 1,975,853 | 10/1934 | Lazier et al. | 560/239 |
| 2,160,064 | 5/1939 | Eversole | 560/239 |
| 4,149,009 | 4/1979 | Yoneoka et al. | 560/239 |

FOREIGN PATENT DOCUMENTS

| 2716842 | 10/1977 | Fed. Rep. of Germany . | |
| 51-65708 | 6/1976 | Japan | 560/239 |
| 53-108916 | 9/1978 | Japan | 560/239 |
| 313575 | 12/1930 | United Kingdom | 560/239 |

Primary Examiner—José G. Dees
Assistant Examiner—Joseph M. Conrad, III
Attorney, Agent, or Firm—Herbert B. Keil

[57] ABSTRACT

Methyl formate is prepared by converting methanol over a copper-containing catalyst at elevated temperatures and in the gas phase by a process in which the catalyst used contains from 30 to 80% by weight of copper, calculated as CuO, as well as from 20 to 70% by weight of a magnesium silicate, calculated as MgO plus SiO$_2$, which has a molar ratio of MgO/SiO$_2$ of from 0.3 to 1.5, and may additionally be doped with the metals zinc, chromium and/or barium, each in an amount of not more than 1.5% by weight, calculated as ZnO, Cr$_2$O$_3$ and BaO.

4 Claims, No Drawings

PREPARATION OF METHYL FORMATE

This application is a continuation application of Ser. No. 07/606,324, filed on Oct. 31, 1990, now abandoned.

The present invention relates to a process for the preparation of methyl formate by dehydrogenating methanol over a copper-containing catalyst at elevated temperatures and in the gas phase.

Methyl formate is for the most part prepared by reacting methanol with carbon monoxide in the presence of an alkali metal alcoholate. To carry out this process in an economical manner, however, it is important for plants for the production and supply of sufficient amounts of carbon monoxide to be located at the methyl formate production site or close to it. However, this is frequently not the case, particularly with smaller chemical production sites, and alternative syntheses for the preparation of methyl formate, which manage without carbon monoxide, for example the dehydrogenation of methanol to methyl formate, are therefore of economic interest for these sites.

The dehydrogenation of methanol to methyl formate has long been known and is disclosed in, for example, U.S. Pat. Nos. 1,400,195, 1,975,853 and 2,160,064. Catalysts of metallic copper, some of them in the form of supported catalysts, are used. However, the cost-efficiency of these processes was unsatisfactory and the processes of these patents have not become established.

Over the past years there have been attempts to make this process more economical by developing novel catalysts. For example, DE-A 27 16 842 describes catalysts for the dehydrogenation of methanol to methyl formate which, in addition to copper, contain one or more elements from one of the groups IIIA, including the rare earth metals, from group IVA and from the actinide group. The content of the relatively rare elements of group IIIA and of the rare earth metals makes these catalysts uneconomical, and the use of actinides as a catalyst component on an industrial scale is unacceptable purely for reasons of radiation protection.

DE-A 27 53 634 describes the dehydrogenation of methanol to methyl formate using copper catalysts which additionally contain zirconium, zinc and, alternatively, aluminum. According to this publication, copper/zinc/zirconium catalysts and copper/zinc/zirconium/aluminum catalysts in which these elements are present in atomic ratios of 1:0.3:0.3 and 1:0.3:0.3:0.1, respectively, are supposed to permit a selectivity of 83.6% and 84.6%, respectively, and methyl formate yields of 48.9% and 62.0%, respectively, in the preparation of methyl formate at 280° C. When these experiments were repeated, however, selectivities of only 2.2% and 43.5%, respectively, and yields of 1.5% and 28.5%, respectively, could be obtained in the best cases with these catalysts in the preparation of methyl formate from methanol. Efficiency of these catalysts is thus insufficient for carrying out this process for the preparation of methyl formate in an economical manner.

It is an object of the present invention to provide a process which permits the preparation of methyl formate by dehydrogenating methanol in an economical manner. For this purpose, it was intended to find and use catalysts which are obtainable in a simple manner from readily and economically available starting materials.

We have found that this object is achieved by a process for the preparation of methyl formate by converting methanol over a copper-containing catalyst at elevated temperatures and in the gas phase, wherein the catalyst used contains from 30 to 80% by weight of copper, calculated as CuO, as well as from 20 to 70% by weight of a magnesium silicate, calculated as MgO plus $SiO_2$, which has a molar ratio of $MgO/SiO_2$ of from 0.3 to 1.5, and may additionally be doped with the metals zinc, chromium and/or barium, each in an amount of not more than 1 5% by weight, calculated as ZnO, $Cr_2O_3$ and BaO.

The catalysts used according to the invention contain, as the main components, copper and a magnesium silicate and may furthermore be doped with small amounts of zinc, chromium and/or barium. The amounts stated below are each based on the prepared catalyst before loss on ignition and before its reduction with hydrogen, unless stated otherwise.

The catalysts employed according to the invention generally have copper contents of from 30 to 80, preferably from 40 to 80, in particular from 60 to 80, % by weight, calculated as CuO. The magnesium silicates are present in these catalysts in amounts of from 20 to 70, preferably from 20 to 60, in particular from 20 to 40, % by weight, calculated as MgO plus $SiO_2$. The catalysts are prepared so that the molar ratio $MgO/SiO_2$ in the catalyst is in general 0.3 to 1.5, advantageously 0.5 to 1.2, preferably 0.6 to 0.9. Furthermore, the catalysts used according to the invention may be doped with not more than 1.5, advantageously from 0.3 to 1.3, in particular from 0.6 to 1.1, % by weight of each of the metals zinc, chromium and/or barium, calculated as ZnO, $Cr_2O_3$ and BaO.

Thus, catalysts which contain only copper and magnesium silicates can be used in the novel process, but catalysts which have been doped with one or more, preferably with all, of the stated other metals within the stated limits can also advantageously be employed.

The catalysts are generally prepared by precipitating magnesium silicate by adding a magnesium salt solution, preferably a magnesium nitrate solution, to an alkali metal silicate solution which is advantageously strongly alkaline, preferably a waterglass solution, the ratios of the salt solutions to be reacted advantageously being chosen so that the precipitate which forms contains magnesium and silicate, calculated as MgO and $SiO_2$, in the desired molar ratio. The precipitate obtained in the reaction of magnesium salt solution with the waterglass solution is X-ray amorphous.

The copper and, if desired, the components zinc, chromium and/or barium in the form of their salt solutions, preferably in the form of their nitrate solutions, are then added to the resulting magnesium silicate suspension, advantageously with stirring. The precipitating agent can be metered into this mixture before or after the addition of this metal salt solution but is advantageously introduced simultaneously with the metal nitrate solutions into the precipitation apparatus. The precipitating agents used are in general aqueous solutions of the hydroxides, carbonates or bicarbonates of the alkali metals. The use of sodium carbonate or potassium carbonate solutions as precipitating agents is particularly preferred. Precipitation may be carried out at room temperature, at elevated temperatures or at the boiling point. It is advantageously effected at from 30° to 70° C.

In the preparation of the catalysts used according to the invention, it is also possible to employ a method in which the magnesium silicate and the other catalyst components are precipitated separately and the resulting precipitates are mixed before or after drying, but the procedure described above, in which the stated catalyst components are precipitated onto the preprecipitated magnesium silicate, is preferred.

In the preparation of zinc-containing catalysts with the use of alkali metal hydroxide solutions as precipitating agents, it is of course necessary to ensure that the precipitated zinc hydroxide does not redissolve as zincate owing to the addition of excessive amounts of alkali metal hydroxide. In the preparation of chromium-containing catalysts, water-soluble chromium(III) salts are preferably used as starting materials.

The generally chemically impure precipitate of the catalyst components which is obtained in this manner consists of a mixture of sparingly soluble hydroxides, carbonates, hydrated oxides and basic salts of the precipitated metal components with the magnesium silicate mixture precipitated beforehand, the composition of said precipitate depending on the precipitating agent used.

The precipitated catalyst components can be separated from the liquid phase in a conventional manner, for example by filtration or centrifuging, and washed and dried. The drying temperature is in general from 80° to 200° C., preferably from 100° to 160° C., in particular from 110° to 130° C. After drying, the catalyst is calcined, in general at from 200° to 500° C. For the preparation of catalyst moldings, the calcined catalyst raw material is advantageously thoroughly mixed with molding assistants, such as graphite or stearic acid, and then pressed to give the desired moldings.

Before they are used for dehydrogenating methanol to methyl formate, the catalysts are advantageously reduced in a stream of hydrogen at elevated temperatures. The hydrogen is preferably used in the form of a gas mixture of hydrogen and an inert gas, such as nitrogen or argon. The reduction of the catalyst is generally carried out at 150° to 250° C. In the reduction, the metal components reducible with hydrogen are reduced to the metals if they come into contact with the reducing agent directly or by diffusion. The catalysts which can be used according to the invention can be employed as a powder or as moldings for the reaction.

For the preparation of methyl formate by the novel process, gaseous methanol is passed over one of the catalysts which can be used according to the invention, in general at from 150° to 300° C., preferably from 200° to 290° C., in particular from 240° to 280° C., and in general at from −0.1 to 10 bar, advantageously at atmospheric pressure, and dehydrogenated to methyl formate.

The reaction is generally carried out continuously in a tube reactor or fluidized-bed reactor. Gaseous methanol is passed over the catalyst bed under the abovementioned reaction conditions at a space velocity of, in general, from 100 to 10000 h$^-$, advantageously at from 3500 to 7000 h$^-$. If desired, the gaseous methanol stream may be diluted with an inert gas, such as argon or, preferably, nitrogen.

For this purpose, the methanol is generally vaporized in an evaporator upstream of the reactor, advantageously in a column, and is brought to the reaction temperature. The catalyst bed can likewise be preheated by heating to the reaction temperature from outside and can be kept at the desired reaction temperature during the reaction.

The reaction mixture which leaves the reactor and consists, in addition to methyl formate, essentially of unconverted methanol, hydrogen and, where relevant, the inert gas can be worked up by a conventional method. Thus, the liquid components of the reaction mixture, i.e. methyl formate and methanol, can be separated off from the gaseous components, i.e. the inert gas, hydrogen and gaseous byproducts, such as carbon monoxide, advantageously by distillation under superatmospheric pressure, in gas/liquid separators. After the separation of the reacted mixture into its liquid and gaseous forms, the methyl formate formed is separated from the unconverted methanol by distillation and is isolated. The methanol recovered can, if desired, be recycled to the reaction or used for other purposes.

By means of the novel process, methyl formate can be prepared in an economical manner by dehydrogenating methanol.

Methyl formate is essentially used for the preparation of formic acid and the various formamides.

EXAMPLES

Catalyst Preparation

Catalyst 1

A strongly alkaline sodium waterglass solution and a magnesium nitrate solution were mixed at 35° C. while stirring, a magnesium silicate precipitate having a molar ratio of MgO/SiO$_2$ of 0.7 being formed. A mixed solution of copper(II) nitrate, zinc nitrate, chromium(II) nitrate and barium nitrate was pumped into the resulting magnesium silicate suspension while stirring and at 55° C. Simultaneously with this solution, sodium carbonate solution was introduced into the suspension. The resulting precipitate was filtered off, washed, and dried at 120° C. It was then calcined at 250° C. until the loss on ignition was about 15% by weight. After admixing 3% by weight of graphite as a molding assistant, the resulting material was pressed to give pellets.

The catalyst prepared in this manner contained 77.4% by weight of copper, calculated as CuO, 0.3% by weight of chromium, calculated as Cr$_2$O$_3$, 0.3% by weight of zinc, calculated as ZnO, 0.4% by weight of barium, calculated as BaO, 7.0% by weight of magnesium, calculated as MgO, and 14.1% by weight of silicate, calculated as SiO$_2$. The bulk density of the catalyst was 820 g/l, and the porosity was 0.39 ml/g, measured as water absorption, and the compressive strength was 4,200 N/cm$^2$.

Catalyst 2

A catalyst was prepared similarly to the process for the preparation of catalyst 1 and had the following chemical composition after calcination and before its reduction:

44.8% by weight of copper, calculated as CuO,
0.7% by weight of chromium, calculated as Cr$_2$O$_3$,
0.5% by weight of zinc, calculated as ZnO,
1.2% by weight of barium, calculated as BaO,
17.7% by weight of magnesium, calculated as MgO, and
35.0% by weight of silicate, calculated as SiO$_2$.

Comparative catalyst A

Comparative catalyst A was obtained according to Example 1 of DE-A 27 16 842, by kneading copper carbonate and zirconium carbonate with water, drying, heating and molding with the aid of 3% by weight of graphite as a molding assistant. The catalyst contained 87% by weight of copper calculated as CuO, and 13% by weight of zirconium, calculated as $ZrO_2$. Its bulk density was 2,110 g/l, its water absorption 0.14 ml/g and its compressive strength 1,610 $N/cm^2$.

Comparative catalyst B

Comparative catalyst B was obtained according to Example 1 of DE-A 27 53 634, by precipitation over zinc nitrate/zirconium acetate solution with sodium carbonate solution, filtration, thorough washing and mixing of the resulting precipitate with copper carbonate, drying, heating and pelletizing. The catalyst contained 56.5% by weight of copper calculated as CuO, 17.3% by weight of zinc, calculated as ZnO, and 26.2% by weight of zirconium, calculated as $ZrO_2$. Its bulk density was 1,461 g/l, the water absorption 0.23 ml/g and its compressive strength 3,000 $N/cm^2$.

Comparative catalyst C

Comparative catalyst C was obtained according to Example 2 of DE-A 27 53 634, by precipitation of a copper nitrate/zinc nitrate solution with sodium carbonate solution, filtration, thorough washing and mixing of the resulting precipitate with aluminum hydroxide and zirconium carbonate, drying, heating and pelletizing. The prepared catalyst contained 50.6% by weight of copper calculated as CuO, 21.9% by weight of zinc, calculated as ZnO, 3.4% by weight of aluminum, calculated as $Al_2O_3$, and 23% by weight of zirconium, calculated as $ZrO_2$. Its bulk density was 1,810 g/l, the water absorption 0.15 ml/g and its compressive strength 4,028 $N/cm^2$.

Preparation of methyl formate

The abovementioned catalysts were comminuted to chips-having a particle size of 1.5 to 1.8 mm. 30 ml of each of these catalysts were introduced into a quartz glass reactor having an internal diameter of 20 mm and reduced with a hydrogen/nitrogen gas mixture (volume ratio of $H_2/N_2$ 2:98) at 200° C. for 16 hours.

Methanol vapor was passed over the reduced catalysts at atmospheric pressure, at the temperatures (T) stated in the Tables and with the stated space velocities (SV).

The composition of the reacted mixture was determined by gas chromatography, and the methanol conversion (C) and the selectivity (S) for methyl formate was calculated from the results of this analysis. The experimental results are listed in Tables 1 to 3.

TABLE 1

Results of methyl formate preparation using catalyst 1

| Temperature °C. | SV $h^{-1}$ | C(MeOH) % | S(Mefo) % |
|---|---|---|---|
| 180 | 5,800 | 6.8 | 98.0 |
| 200 | 6,062 | 14.1 | 83.3 |
| 220 | 6,319 | 17.8 | 99.0 |
| 240 | 6,575 | 26.3 | 94.2 |
| 260 | 6,831 | 36.2 | 87.4 |

TABLE 1-continued

Results of methyl formate preparation using catalyst 1

| Temperature °C. | SV $h^{-1}$ | C(MeOH) % | S(Mefo) % |
|---|---|---|---|
| 260 | 5,960 | 42.7 | 75.6 |

MeOH: methanol
Mefo: methyl formate

TABLE 2

Results of methyl formate preparation using catalyst 2

| Temperature °C. | SV $h^{-1}$ | C(MeOH) % | S(Mefo) % |
|---|---|---|---|
| 160 | 3,600 | 20.8 | 75.3 |
| 180 | 3,871 | 29.9 | 71.1 |
| 200 | 4,042 | 36.1 | 55.0 |
| 220 | 4,213 | 41.0 | 48.1 |
| 180 | 5,807 | 27.0 | 92.3 |
| 200 | 6,068 | 35.9 | 66.1 |

TABLE 3

Results of methyl formate preparation using comparative catalysts A, B and C

| Comparative catalyst | Temperature °C. | SV $h^{-1}$ | C(MeOH) % | S(Mefo) % |
|---|---|---|---|---|
| A | 180 | 2,700 | 3 | 55 |
| A | 200 | 2,830 | 2.4 | 87.2 |
| A | 220 | 2,940 | 1.6 | 76.0 |
| A | 240 | 3,040 | 4 | 12.9 |
| A | 260 | 3,190 | 4.1 | 38.1 |
| A | 280 | 3,310 | 8 | 60 |
| A | 300 | 3,410 | 14.1 | 69.3 |
| A | 310 | 3,460 | 19.1 | 72.7 |
| B | 180 | 3,900 | 1.6 | 81.4 |
| B | 200 | 4,150 | 3.1 | 82.7 |
| B | 240 | 4,430 | 6.1 | 90.1 |
| B | 260 | 4,650 | 27.3 | 78.7 |
| B | 280 | 4,820 | 43.3 | 74.7 |
| B | 300 | 5,080 | 62.1 | 31.4 |
| B | 310 | 5,210 | 77.0 | 16.5 |
| C | 240 | 6,600 | 16.3 | 76.0 |
| C | 260 | 7.060 | 24.2 | 57.9 |
| C | 280 | 7,270 | 36.9 | 32.9 |
| C | 300 | 7,380 | 49.1 | 15.7 |
| C | 310 | 7,470 | 53.3 | 5.9 |

We claim:

1. A process for the preparation of methyl formate by dehydrogenating methanol over a copper-containing catalyst at elevated temperatures and in the gas phase, wherein the catalyst used contains from 30 to 80% by weight of copper, calculated as CuO, as well as from 20 to 70% by weight of a magnesium silicate, calculated as MgO plus $SiO_2$, which has a molar ratio of $MgO/SiO_2$ of from 0.3 to 1.5, and may additionally be doped with the metals zinc, chromium and/or barium, each in an amount of not more than 1.5% by weight, calculated as ZnO, $Cr_2O_3$ and BaO.

2. A process as claimed in claim 1, wherein the methanol is passed over the catalyst at from 150° to 300° C. and at from 0.1 to 10 bar.

3. A process as defined in claim 1, wherein the catalyst contains from 60 to 80% by weight of copper, calculated as CuO, from 20 to 40% by weight of a magnesium silicate, calculated as MgO plus $SiO_2$ and wherein the molar ratio of $MgO/SiO_2$ is from 0.6 to 0.9.

4. A process as defined in claim 3, wherein the catalyst is doped with from 0.6 to 1.1% by weight of each of the metals zinc, chromium and barium.

* * * * *

UNITED STATES PATENT AND TRADEMARK OFFICE
CERTIFICATE OF CORRECTION

PATENT NO. : 5,194,675

DATED : March 16, 1993

INVENTOR(S) : JOERG et al.

It is certified that error appears in the above-identified patent and that said Letters Patent is hereby corrected as shown below:

ON THE COVER PAGE

Section [30], Foreign Priority Data, the number of the priority document should read --3936854--.

Signed and Sealed this

Twenty-third Day of November, 1993

*Attest:*

BRUCE LEHMAN

*Attesting Officer*     *Commissioner of Patents and Trademarks*